US006386014B1

(12) United States Patent
Butch

(10) Patent No.: US 6,386,014 B1
(45) Date of Patent: May 14, 2002

(54) ENERGY MEASUREMENT DEVICE FOR FLOWING GAS USING MICROMINIATURE GAS CHROMATOGRAPH

(75) Inventor: James N. Butch, Charleston, WV (US)

(73) Assignee: Eagle Research Corporation, Scott Depot, WV (US)

( * ) Notice: Subject to any disclaimer, the term of this patent is extended or adjusted under 35 U.S.C. 154(b) by 0 days.

(21) Appl. No.: 09/442,726

(22) Filed: Nov. 18, 1999

(51) Int. Cl.$^7$ .............................................. G01N 30/02
(52) U.S. Cl. .................... 73/23.35; 73/23.22; 73/23.24; 73/23.25; 73/23.27; 73/23.4
(58) Field of Search .............................. 73/23.22, 23.24, 73/23.25, 23.27, 23.35, 23.4, 1.03, 1.06

(56) References Cited

U.S. PATENT DOCUMENTS

| 3,824,838 | A | * | 7/1974 | Ohtsu et al. ............... 73/23.22 |
| 4,094,187 | A | * | 6/1978 | Navarre, Jr. ................. 73/1.03 |
| 4,345,463 | A | | 8/1982 | Wilson et al. .............. 73/23.35 |
| 4,471,647 | A | | 9/1984 | Jerman et al. ............... 73/23.4 |
| 4,935,040 | A | * | 6/1990 | Goedert ...................... 73/23.22 |
| 5,313,061 | A | * | 5/1994 | Drew et al. .................. 250/281 |
| 5,524,473 | A | * | 6/1996 | Haskell ....................... 73/1.03 |
| 5,551,282 | A | * | 9/1996 | Vander Heyden .......... 73/30.03 |
| 5,583,281 | A | | 12/1996 | Yu ............................. 73/23.42 |
| 5,699,157 | A | | 12/1997 | Parce |
| 5,707,150 | A | | 1/1998 | Sittler ......................... 374/36 |
| 5,779,868 | A | | 7/1998 | Parce et al. |
| 5,800,690 | A | | 9/1998 | Chow et al. |
| 5,842,787 | A | | 12/1998 | Kopf-Sill et al. |
| 5,852,495 | A | | 12/1998 | Parce |
| 5,869,004 | A | | 2/1999 | Parce et al. |
| 5,876,675 | A | | 3/1999 | Kennedy |
| 5,880,071 | A | | 3/1999 | Parce et al. |
| 5,882,465 | A | | 3/1999 | McReynolds |
| 5,885,470 | A | | 3/1999 | Parce et al. |
| 5,900,130 | A | | 5/1999 | Benvegnu et al. |
| 5,942,443 | A | | 8/1999 | Parce et al. |
| 5,948,227 | A | | 9/1999 | Dubrow |
| 5,955,028 | A | | 9/1999 | Chow |
| 5,957,579 | A | | 9/1999 | Kopf-Sill et al. |
| 5,958,203 | A | | 9/1999 | Parce et al. |
| 5,958,694 | A | | 9/1999 | Nikiforov |
| 5,959,291 | A | | 9/1999 | Jensen |

(List continued on next page.)

FOREIGN PATENT DOCUMENTS

| SU | 1122967 | * | 11/1984 | ................ 73/23.41 |
| SU | 1392501 | * | 4/1988 | ................ 73/24.41 |

Primary Examiner—Daniel S. Larkin
(74) Attorney, Agent, or Firm—MacCord Mason PLLC

(57) ABSTRACT

A system for determining the energy and volume delivered by a flowing natural gas carried within a pipeline based on BTU content analysis of the natural gas using a microminiature gas chromatograph. By monitoring key parameters of the flowing natural gas, such as temperature, pressure, flow rate, and BTU content, the system 110 accurately determines the total energy and total volume delivered by the flowing natural gas over a programmable duration of time. Micro-miniature fabrication of the gas chromatograph imparts important advantages to the system 110, including small size, modular design, low power consumption, fast BTU analysis times, and low consumption of consumable carrier and reference gases. Low power consumption permits operation of the system 110 using low-capacity supplies such as solar or battery, while minuscule consumption of consumable gases permits the use of 100 ml or less cartridges for the carrier and reference gases, making the integration of the consumable gas cartridges into the system 110 enclosure practical. A further advantage of the micro-miniature gas chromatograph as used in the system 110 is its modular design, allowing convenient disposal and replacement. The foregoing attributes combine to provide an energy monitoring system that, due to its small size, low operating power, and low consumption of consumable gases, is ideally suited for unattended operation for extended periods of time.

37 Claims, 9 Drawing Sheets

U.S. PATENT DOCUMENTS 5,964,995 A    10/1999   Nikiforov et al.
5,965,001 A    10/1999   Chow et al.
5,965,410 A    10/1999   Chow et al.
6,114,964 A *  9/2000    Fasano ...................... 73/31.02

* cited by examiner

ENERGY MEASUREMENT DEVICE FOR FLOWING GAS USING MICROMINIATURE GAS CHROMATOGRAPH

FIELD OF THE INVENTION

The present invention generally relates to natural gas measurement, and particularly relates to determining energy, based on BTU analysis, associated with natural gas flowing in a pipeline.

BACKGROUND OF THE INVENTION

Pipeline delivery of natural gas requires accurate measurement of the volume of gas delivered to a given point in the distribution system. However, simply determining the volume of gas delivered over a given interval of time is inadequate for determining the economic value associated with that volume of gas. Because natural gas represents a source of energy, its real value depends on the amount of energy actually contained in a given volume of gas. The British Thermal Unit represents a common unit of measure for the amount of energy contained in natural gas. As natural gas typically varies between 900 and 1,200 BTU/ft$^3$, the total amount of energy contained in a given volume of natural gas varies appreciably. Therefore, large-scale consumers and distributors of natural gas have an economic interest in determining the actual energy value of the natural gas used or transported by their facilities.

Several parameters are all necessary to accurately determine total volume and total energy associated with a gas flowing in a pipeline over a given interval of time, including temperature, pressure, supercompressibility, and BTU content. Existing natural gas measurement systems typically monitor a subset of these parameters and assume constant or defined values for the remaining parameters. BTU content, because of the complexity associated with its accurate determination, is typically not directly measured and energy content calculations use an assumed value. For significant volumes of natural gas, however, a fixed-value assumption for BTU content yields inaccuracies of appreciable economic value. Natural gas is itself comprised of a number of constituents and accurate determination of its BTU content requires identification of one or more of these key constituents. Simple calorimeter techniques are unsatisfactory for identifying the constituent makeup of the monitored gas flow. Gas chromatography offers superior analytical capability when compared to simple calorimeter techniques, at the expense of greater cost, size, and power. Indeed, present gas chromatograph systems adapted to measurement of natural gas BTU content are large, expensive, and require appreciable quantities of reference and carrier gases for analysis, resulting in significant maintenance requirements.

Accordingly, there remains a need for a small and inexpensive energy measurement system employing gas chromatography adapted for accurately determining the total energy and total volume associated with a natural gas flowing within a pipeline. The present invention addresses this need by advantageously employing a micro-miniature gas chromatograph for determination of natural gas BTU content. By further including the ability to directly monitor other critical flow parameters, the present invention provides an integrated apparatus for determining natural gas volume and energy measurement.

SUMMARY OF THE INVENTION

The present invention provides an energy measurement system for monitoring a natural gas flowing within a pipeline to accurately determine a total volume and total energy associated with the flowing gas over a given interval of time. By employing a micro-miniature gas chromatograph, the present invention accurately determines the BTU content of the monitored natural gas. By additionally monitoring other critical flow parameters of the natural gas, such as temperature, pressure, and flow rate, the present invention determines total volume and total energy delivered by the flowing natural gas. Employing micro-miniature technology, the gas chromatograph of the present invention has greatly reduced size and operating power requirements and uses only minute quantities of both carrier and reference gases. These characteristics of the micro-miniature gas chromatograph impart specific advantages to the overall system, such as the ability to operate from small solar panels or reduced capacity battery cells. Further, the minute quantities of carrier gas used, typically less than one micro-liter per BTU analysis, permit the use of gas canisters small enough to be integrated into the electronic enclosure. A further advantage of micro-miniature technology is the high level of integration that permits implementation of the gas chromatograph as a small, easily replaceable modular assembly.

The foregoing attributes combine to yield an energy analysis system providing small size, low operating power, and low consumption of consumable gases, resulting in a system suitable for remote, unattended installation with low maintenance requirements. Details and advantages of the present invention are made clear through explanatory text and by reference to drawings illustrating particular features of the system. Further although presented in the context of natural gas analysis, the present invention may be advantageously applied to many other fuel gas compositions.

DETAILED DESCRIPTION OF THE INVENTION

Figure 1:
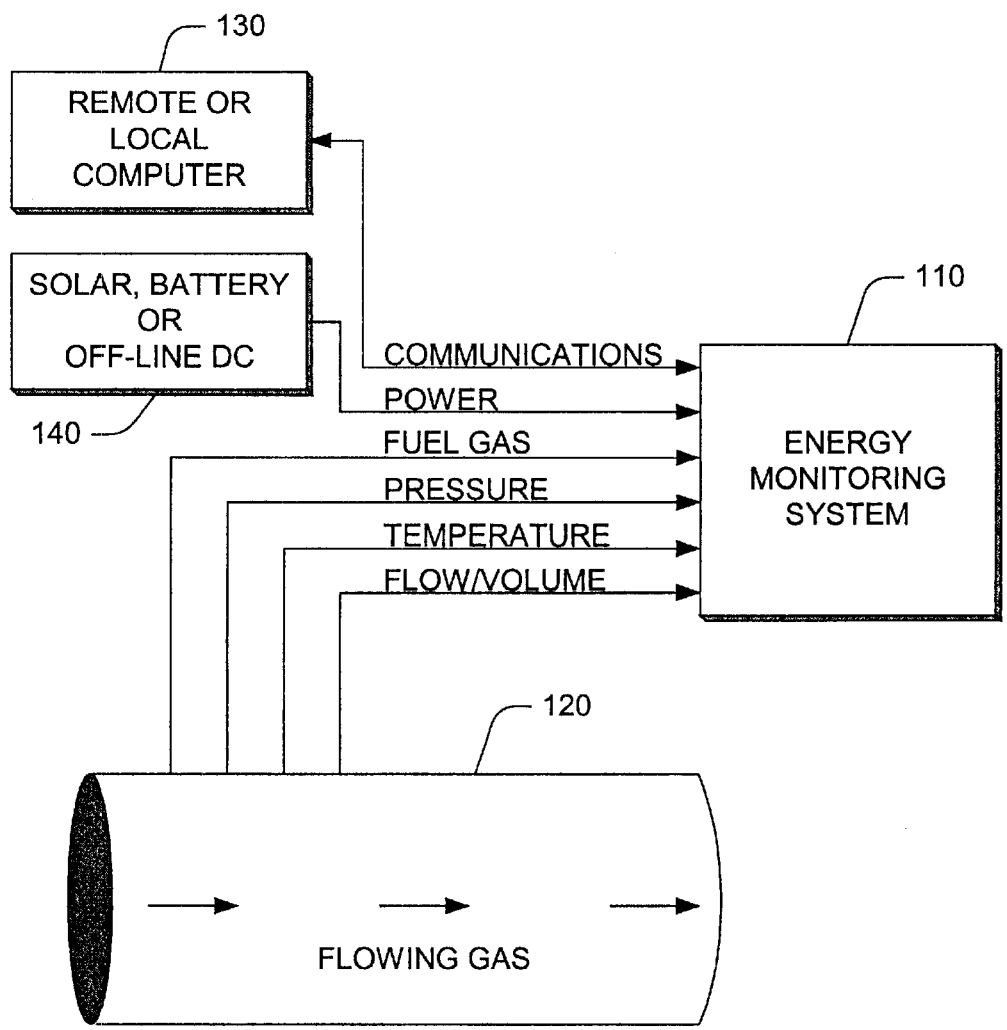
FIG. 1 is a simplified block diagram of the present invention interfaced with a pipeline containing flowing natural gas.

The composition and, therefore, the heating value, of natural gas flowing within a distribution pipeline varies appreciably over time. The table below details typical natural gas composition:

| Typical Natural Gas Composition | | |
|---|---|---|
| Methane | $CH_4$ | 70%–90% |
| Ethane | $C_2H_6$ | |
| Propane | $C_3H_8$ | 0%–20% |
| Butane | $C_4H_{10}$ | |
| Carbon dioxide | $CO_2$ | 0%–8% |
| Oxygen | $O_2$ | 0%–0.2% |
| Nitrogen | $N_2$ | 0%–5% |
| Hydrogen sulphide | $H_2S$ | 0%–5% |

Certain trace gases not listed above are contained in natural gas in negligible amounts and natural gas additionally contains entrained moisture.

Accurate determination of the total energy associated with the flowing natural gas must be based on BTU content analysis, determined from repeated measurements made at appropriate time intervals. Gas chromatography provides a mechanism for accurate constituent analysis of natural gas because its separation capability allows identification of multiple natural gas constituents including non-combustibles, saturated hydrocarbons, and unsaturated hydrocarbons.

In gas chromatography, a separation column is filled or coated with a liquid or solid "stationary phase." An inert carrier gas or "mobile phase" is injected along with a sample gas into a heated injection chamber and carries the sample gas through the heated separation column wherein the different molecules of the sample gas are adsorbed into the stationary phase. The length of time spent in the separation column by the different compounds comprising the sample gas depends on their tendency to be adsorbed. Therefore, the different compounds within the sample gas separate as they move through the separation column at different rates of travel. A detector placed at the end of the separation column is used to detect the separated compounds as they exit the separation column. As the detector principally responds to compounds in the sample gas and not the carrier gas, the detection response comprises a series of time-displaced peaks corresponding to the separated constituent compounds of the sample gas. The time displacement of a peak in the detector response corresponds to the compound identity and the area under the peak in the response curve corresponds to the amount of constituent. Therefore, mole % constituent concentration for the sample gas can be determined using gas chromatograph analysis and this is important for accurately determining energy content.

Conventional gas chromatographs typically use a "packed" separation column fabricated from steel tubing and filled with adsorbent material. These separation columns are usually coiled and have an overall length exceeding ten meters or more. Because of the physical size of the separation column and the need to heat the separation column assembly and associated injection port, conventional gas chromatographs are relatively large and expensive. Typical weights for conventional gas chromatographs can exceed 30 Kg, and they can easily cost in excess of $10,000. Further, because of the need to heat a large separation column, conventional gas chromatographs require significant operating power, precluding the use of small solar panels or low-capacity battery cells to power them. These size, cost, and power disadvantages, combined with the need for appreciable quantities of carrier and reference gas in normal operation, limit the usefulness of gas chromatography for on-line analysis of natural gas energy. The application of micro-miniature technology to the fabrication and construction of gas chromatography systems overcomes these limitations. Micro-miniature gas chromatographs offer a further advantage over conventional gas chromatographs in terms of analysis speed. Analysis time can be less than one minute using a micro-miniature gas chromatograph, while conventional gas chromatographs typically require in excess of five to ten minutes to perform a comparable analysis.

In micro-miniature technology, mechanisms are implemented on a micro-scale using photolithography and laser etching techniques. Micro-miniature techniques borrow from methods developed and refined in the production of silicon microelectronics. Indeed, micro-miniature systems may be implemented within silicon in a manner similar to electronic microchips. In general, these micro-miniature systems are formed as laminate structures and integrate micro-machined electromechanical elements (MEMs) and fluid transport channels, along with control and sensor electronics. Caliper Technologies Corporation, having a business address at 605 Fairchild Drive, Mountain View, Calif. 94043-2234, and a web site at www.calipertech.com, has developed sophisticated micro-fluidic systems suitable for use in a micro-miniature gas chromatograph. Caliper Technologies holds a series of U.S. Patents related to its micro-fluidic systems, including U.S. Pat. Nos. 5,965,410, 5,965,001, 5,964,995, 5,959,291, 5,958,694, 5,958,203, 5,957,579, 5,955,028, 5,948,227, 5,942,443, 5,885,470, 5,882,465, 5,880,071, 5,876,675, 5,869,004, 5,852,495, 5,842,787, 5,800,690, 5,779,868, and 5,699,157, and the disclosures for all these patents are incorporated herein by reference.

General Operation

FIG. 1 depicts the present invention connected to a pipeline carrying a flowing natural gas. If flow rate and pressure are known for the flowing natural gas, then the amount of natural gas delivered through the pipeline over a given period of time may be calculated. Further, by measuring the BTU content of the flowing gas over the same given period of time, the total amount of energy contained in the calculated volume may be determined. The energy and flow measurement system 110 of the present invention monitors a flowing natural gas carried in a pipeline 120 for the purpose of determining total energy and volume delivered through the pipeline over defined intervals of time. The system 110 may monitor pressure, temperature, flow rate, and BTU content of the flowing natural gas to accurately determine total energy and total volume associated with the flowing natural gas. The system 110 supports local and remote communications so that energy, volume, and other key operational data is available to associated monitoring and control systems.

In operation, the system 110 executes a stored computer program that provides monitoring of the critical flow parameters, including temperature, pressure, BTU content, and associated total energy and volume values. Monitored data is stored at programmable intervals and is accessible to other electronic systems 130 either locally or remotely through the communications link. Various aspects of program information may be configured by the end user to compliment operation at a given installation. Configurable parameters include but are not limited to BTU analysis sampling interval, and volume and energy accumulation intervals.

Figure 2:
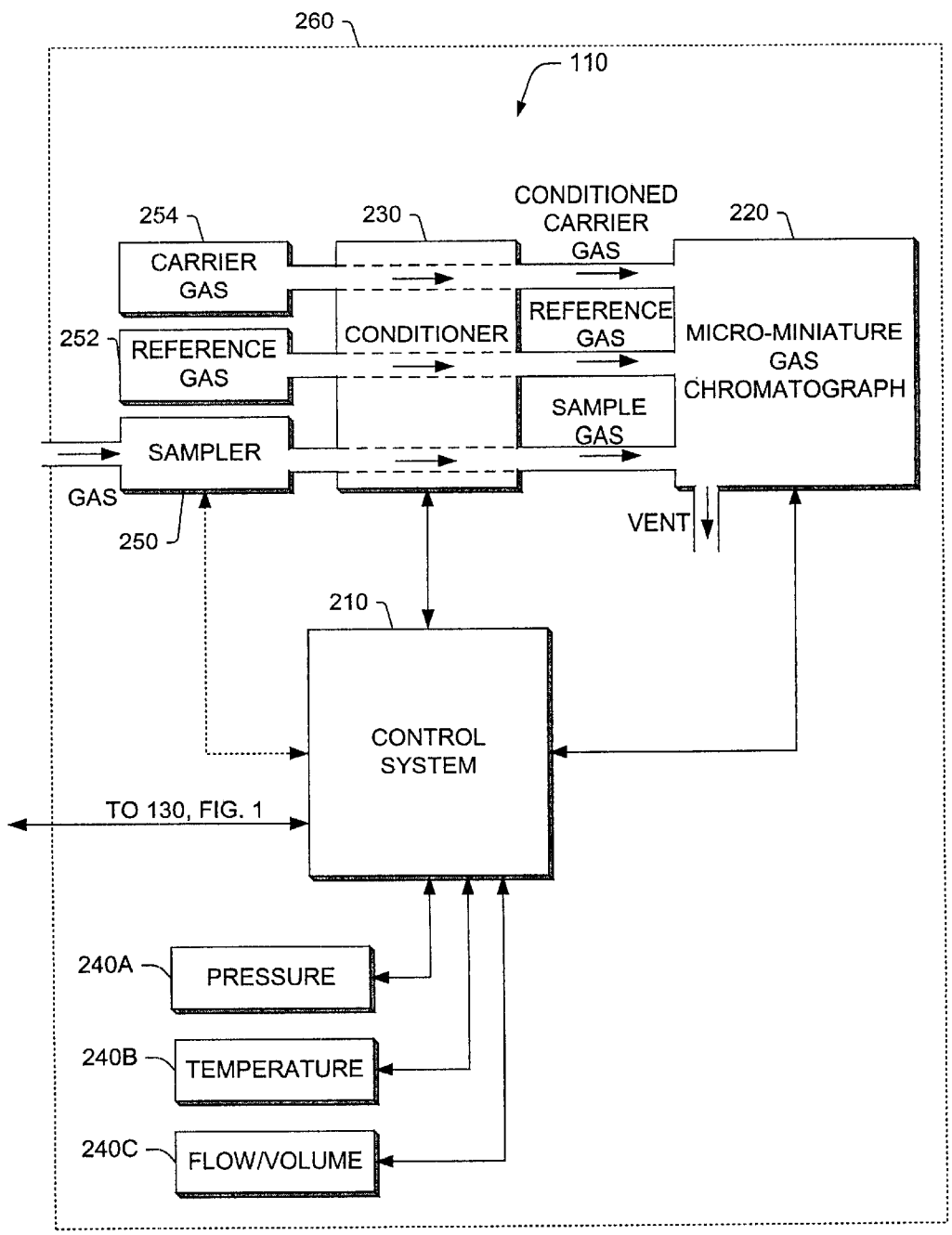
FIG. 2 is a more detailed block diagram of the present invention.

Referring to FIG. 2, a control system 210 provides control and communication functions for the energy and flow measurement system 110. The control system 210 receives signals from a plurality of monitors, including pressure monitor 240A, a temperature monitor 240B, and a flow or volume monitor 240C. By monitoring signals output by these monitors overtime, the control system accurately accumulates volume associated with the flowing natural gas.

As natural gas is compressible, the accumulated volume must be compensated as a function of its temperature and pressure. Because of supercompressibility, this compensation is of particular importance at higher pressures. The American Gas Association (AGA) publishes standardized compensation formulas for supercompressibility, such as the AGA-8 Gross Characterization Method, which requires at least partial constituent analysis of the monitored natural gas. The energy and flow measurement system 110 includes a micro-miniature gas chromatograph 220 for mole % constituent analysis of the flowing natural gas. In the preferred embodiment the energy monitoring system of the present invention may detect a plurality of natural gas constituents, including nitrogen, carbon dioxide, methane, ethane, propane, iso-butane, normal butane, iso-pentane, and normal pentane. Hydrocarbon groups C1 through C5 are individually separated, while C6–C10 are detected as a group. Alternate embodiments of the present invention may be practiced with different separation capabilities.

Power supply 140 provides operating power for the system 110. As noted, use of the micro-miniature gas chromatograph in the energy monitoring system 110 significantly reduces its operating power requirements. The combination of the control system, micro-miniature gas chromatograph and flow meter requires less than 2W of power in operation. More specifically, the micro-miniature gas chromatograph reduces operating power because its small size greatly reduces the amount of energy required to heat its micro-capillary injection chamber and micro-capillary separation column. Further, the micro-miniature gas chromatograph's small size substantially reduces its thermal mass, therefore it heats and cools quite rapidly in comparison to conventional gas chromatographs. As such, warm-up time in advance of gas separation operations using the micro-miniature gas chromatograph is greatly reduced. The preferred embodiment of the present invention additionally includes stand-by and sleep modes of operation in which the energy monitoring system 110 configures its various subsystems for reduced-power operation when not actively engaged in monitoring or analyzing the flowing gas. The control system 210 is configured to periodically operate in a wake state to calculate the energy value of the flowing gas and an ultra-low power sleep state between wake states. Therefore, the power supply 140 may be a solar panel and battery combination, or simply a stand-alone battery. The solar panel may be used for supplying power for operation and to charge the battery. Alternate embodiments of the present invention may also use DC-DC supplies or various types of mains-powered AC-DC supplies.

Detailed Operation

In FIG. 2, in the preferred embodiment of the present invention, the control system 210 includes processing and control functions for oversight and control of the various subsystems comprising the energy and flow measurement system 110. Further, the control system 210 preferably includes a system microprocessor, volatile and non-volatile memory associated with the system processor, analog and digital interfaces associated with the system processor for interfacing with various subsystem blocks, and a communications processor associated with the system processor for providing system monitoring and data access. Because of its use of a micro-miniature gas chromatograph 220, the energy monitoring system of the present invention has greatly reduced size and can include all its various subsystems and components within a common environmental enclosure 260. This includes incorporation of containers for both a carrier and a reference gas used by the micro-miniature gas chromatograph 220 within the enclosure 260.

The control system 210 controls operation of the micro-miniature gas chromatograph 220. For BTU content analysis of the flowing natural gas, the control system 210 cooperates with a fuel sampler 250 to obtain a fresh quantity of the flowing natural gas, referred to as a "sample gas." The sample gas and a quantity of a carrier gas pass through a conditioner 230 and are admitted into the micro-miniature gas chromatograph 220, where the sample gas is separated into its constituents. The control system 210 interfaces with the micro-miniature gas chromatograph 220 to receive information related to one or more constituent gases detected in the micro-miniature gas chromatograph 220. For calibration and testing of the micro-miniature gas chromatograph 220, the control system causes the micro-miniature gas chromatograph 220 to admit conditioned carrier gas in combination with a conditioned reference gas having a known composition. Because the composition of the reference gas is known by the control system 210 a priori, the control system expects a specific detection response from the micro-miniature gas chromatograph 220 and can record any deviations from this expected response.

BTU content analysis of the flowing natural gas requires a fresh sample taken from the natural gas flow within the pipeline. The control system cooperates with a natural gas sampler 250 to obtain this fresh sample of flowing natural gas. The sampler 250 includes design elements to insure that each BTU analysis cycle uses fresh sample gas and provides indication to the control system 210 if ft is unable to obtain a fresh sample. The sampler 250 preferably draws natural gas from the central ⅓ of the flowing natural gas and includes initial pressure regulation such that it provides sample gas to the remainder of the system 110 at a constant, regulated pressure independent of the natural gas pressure in the pipeline. The sampler 250 is preferably designed to withstand excess line pressures in a manner that prevents exposing the remainder of the system 110 to high-pressure gas and additionally prevents venting high-pressure gas to the atmosphere. The sample gas flows through the conditioner 230 where it is preferably filtered. The conditioner 230 may optionally provide additional or secondary pressure regulation, depending upon the regulation characteristics of the sampler 250. In other embodiments of the present invention, the sampler 250 is heated to prevent condensation in its gas flow path and interconnects between the pipeline and the conditioner 230.

Figure 6:
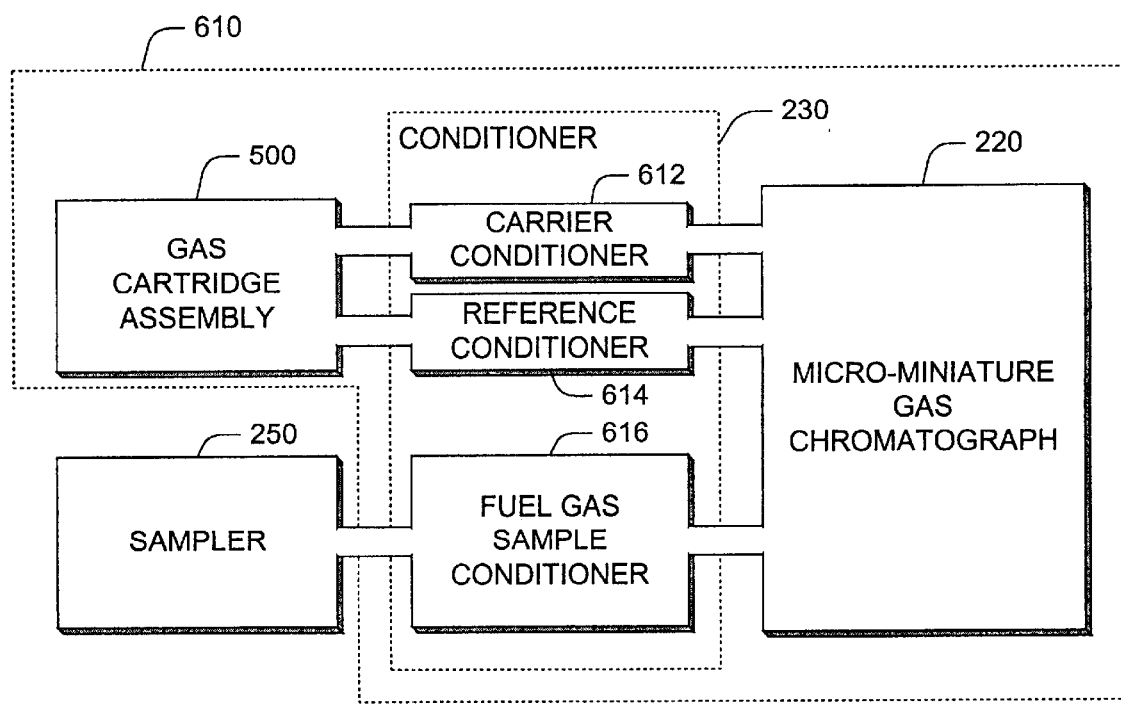
FIG. 6 is a simplified block diagram illustrating the modularity of the present invention in its preferred embodiment.
Figure 7:
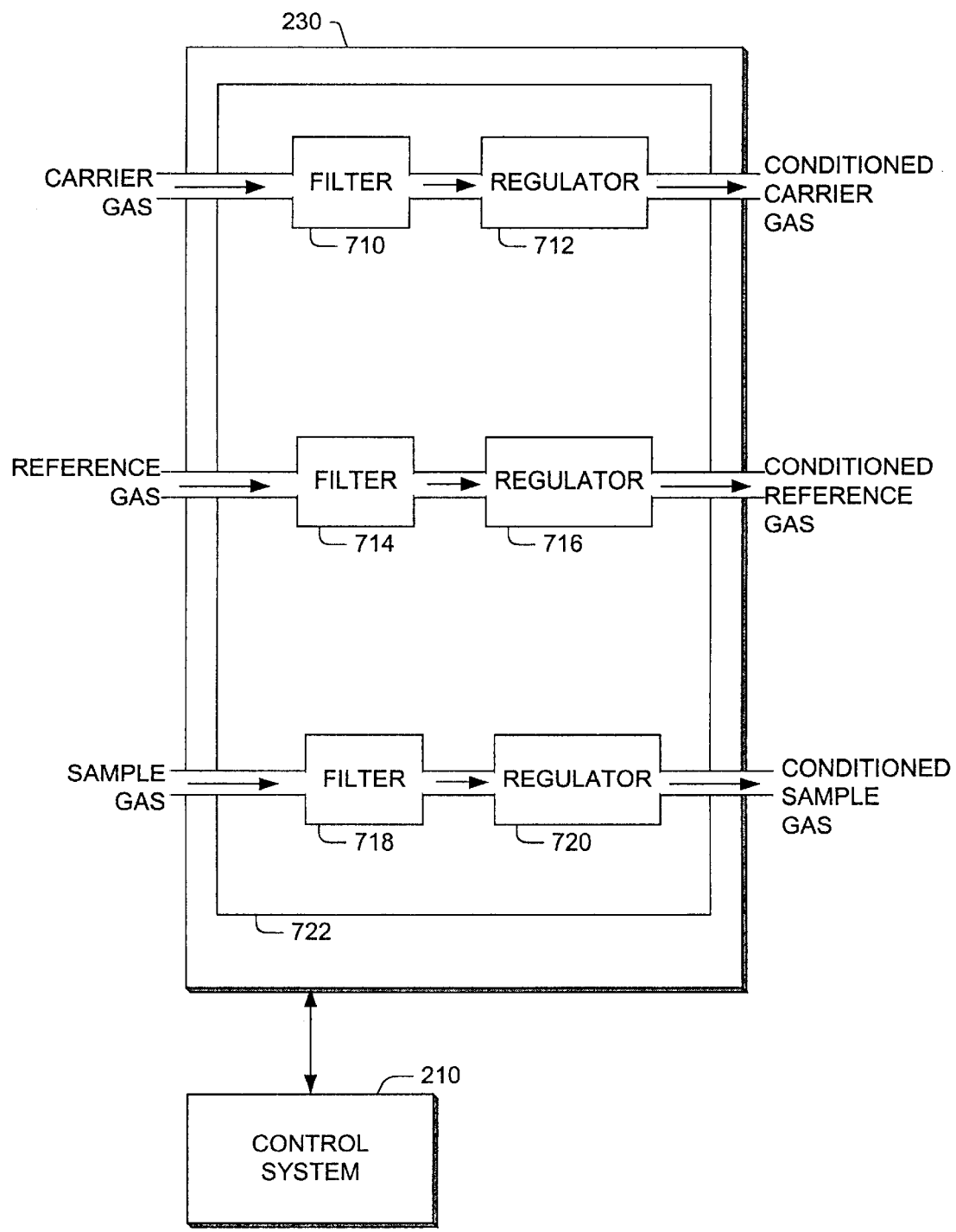
FIG. 7 is a simplified block diagram of the conditioner in the preferred embodiment of the present invention.

The conditioner 230 interfaces with a carrier gas container 254, a reference gas container 252, and the natural gas sampler 250. Carrier gas container 254 provides a pressurized carrier gas to the conditioner 230, the reference gas container provides a pressurized reference gas to the conditioner 230, and the sampler 250 provides sample gas to the conditioner 230. FIGS. 6 and 7 present simplified block diagrams of the conditioner in the preferred embodiment of the present invention. The conditioner includes a carrier gas conditioner 612 further including a carrier gas filter 710 and a carrier gas pressure regulator 712 for providing "conditioned" carrier gas to the micro-miniature gas chromatograph 220. Similarly, the conditioner includes a reference gas conditioner 614, which provides a filter 714 and regulator 716 for the reference gas and a fuel gas sampler conditioner 616, which includes a filter 718 and regulator 720 for the sample gas. The conditioner also includes a heater 722 for preventing condensates from forming within the conditioner. Alternate embodiments omit the heater 722 and may omit the filter 718 and pressure regulator 720 associated with the gas sample, depending upon the specific implementation of the gas sampler 250. These and other variations of the preferred embodiment are considered within the scope of the present invention. The primary purpose of the conditioner 230 is to provide the micro-miniature gas chromatograph 220 with carrier, reference and sample gases that are filtered and maintained at controlled pressures. Gas output from the conditioner 230 to the micro-miniature gas chromatograph 220 is termed "conditioned" gas. In the preferred embodiment, the conditioner 230 additionally provides flow and pressure indicators for the carrier, reference, and sample gases that can be monitored by the control system 210. In this manner, the control system 210 may give advance notice of flow or pressure problems to local or remote service personnel through its communications link. Such data is helpful in monitoring the rate of consumption of reference and carrier gases and allows anticipation of field service requirements.

As detailed earlier, for natural gas BTU content analysis, the control system 210 controls the admission of conditioned sample gas and carrier gas into the micro-miniature gas chromatograph 220. The micro-miniature gas chromatograph 220 separates the sample gas into its constituents and produces an output response based on detection of a plurality of these constituents. Signaling between the micro-miniature gas chromatograph 220 and the control system 210 regarding detected constituents may be either analog or digital, depending upon the level of integration included within the micro-miniature gas chromatograph 220.

As noted, the system 110 of the present invention monitors key flow parameters to determine an energy value associated with the flowing gas. Specifically, the system 110 determines a volume associated with the flowing gas over an interval of time based on its monitoring of pressure, temperature, and flow rate. In simplified terms, the system 110 monitors flow rate over time to calculate the volume of gas delivered through the pipeline. The flow rate of the flowing gas may be obtained in a number of ways. Flow rate is, in the preferred embodiment, derived from the instrument drive interface of a conventional mechanical gas meter, such as are common in the art. In positive displacement gas meters of this type, a mechanical output drive member spins or rotates as gas flows through the meter. Therefore, each rotation of the drive member equates to a unit volume of gas. The system 110 records the number of output drive member rotations and multiples the known unit volume by accumulated number of rotations to determine total volume. For some positive displacement meters, output drive is adjusted to compensate for the pressure of the gas flowing through it, on other types, the output drive reports uncompensated volume. The system 110 of the present invention may be adapted to operate with both compensated and uncompensated positive displacement meters.

Flow rate measurement based on differential pressure is also quite common in the art of pipeline gas transportation, and in an alternate embodiment of the present invention, the differential pressure measured across a known restriction disposed within the natural gas flow, such as an orifice plate, is used to determine the rate of flow of natural gas within the pipeline. In this embodiment, the energy monitoring system includes a differential pressure transducer and interface. Various other electrical, optical, and mechanical apparatus provide measurement of flow rate and all such apparatus are within the scope of the present invention.

Because the density of gas varies with temperature and pressure, and because of supercompressibility phenomenon, the system 110 uses its measurements of flowing gas pressure and temperature to compensate the calculated volume to produce a compensated volume. Through its periodic measurements of BTU content, the system 110 accurately computes an energy value based on this compensated volume.

Micro-miniature Gas Chromatograph

As detailed, the micro-miniature gas chromatograph 220 of FIG. 2 provides the system 110 with the capability to calculate the BTU content of the flowing natural gas based on constituent analysis. Unlike alternate analysis methods, including simple calorimeter or "burning" techniques, gas chromatography permits mole % analysis of the constituents comprising the natural gas. With mole % constituent analysis, the system 110 can accurately compensate for supercompressibility and BTU content.

Implemented using micro-miniature technology, the micro-miniature gas chromatograph 220 represents a highly integrated mechanism for gas chromatography operations and is adapted for operation with minute quantities of carrier, reference, and sample gases. On a per analysis cycle basis, the quantity of carrier gas used is typically less than a microliter. Reference gas is consumed in similarly minute quantities during calibration activities. This low consumption of consumable gases permits extended operation with only small quantities of stored carrier and reference gases. As such, the containers for the carrier and reference gases may be made small enough to fit within the same enclosure used to house the electronic systems comprising the energy flow and measurement system 110.

Figure 3:
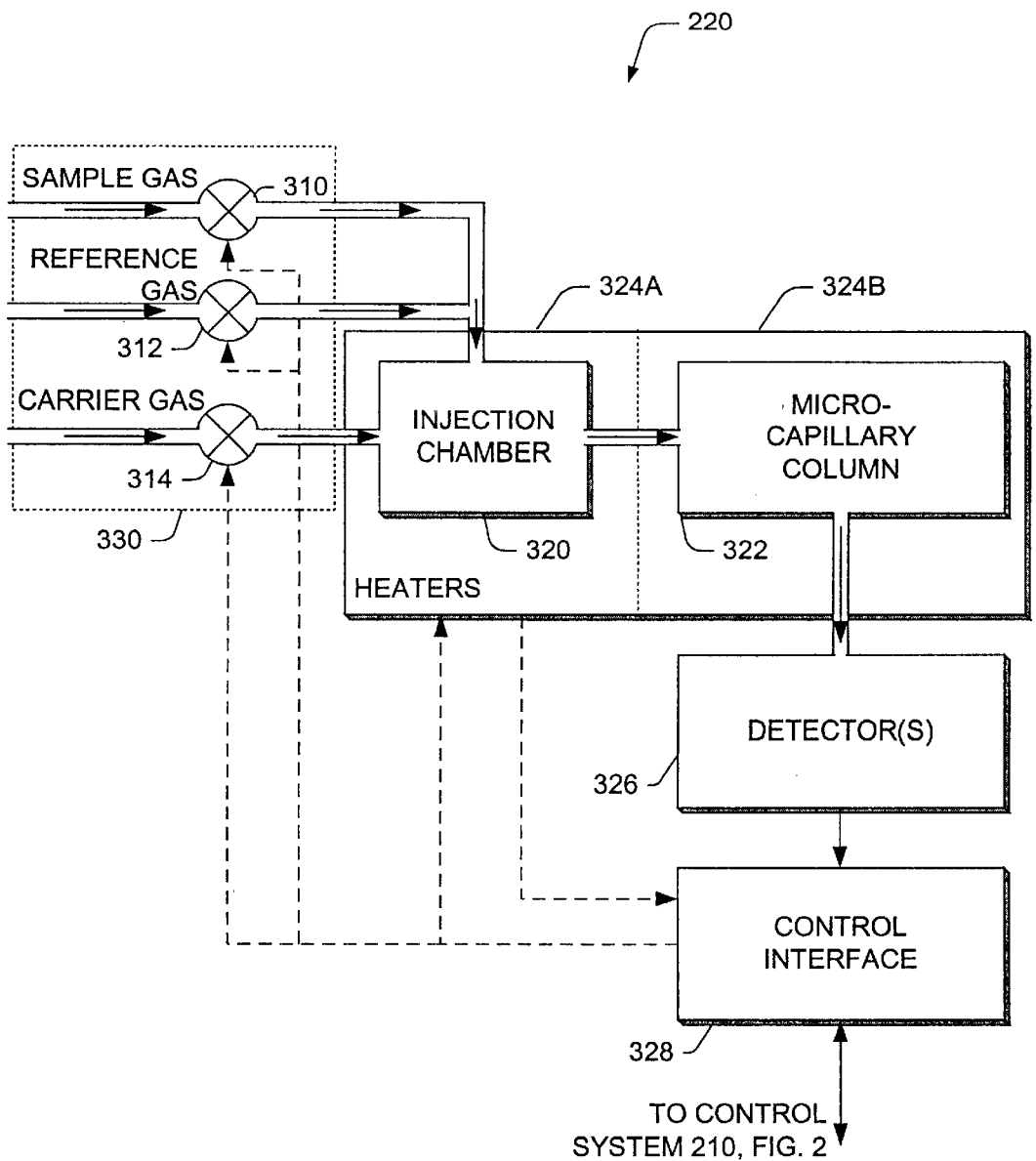
FIG. 3 is a simplified block diagram of the micro-miniature gas chromatograph of the present invention.

FIG. 3 presents additional details related to the micro-miniature gas chromatograph 220. As previously noted, the micro-miniature gas chromatograph 220 is preferably implemented using micro-fabrication techniques such as those developed by Caliper Technologies, Inc. Micro-miniature fabrication permits the construction of gas transport channels within the micro-structures comprising the gas chromatograph having cross-sectional dimensions on the order of one hundred micrometers or less. Using micro-fabrication techniques, the micro-miniature gas chromatograph 220 preferably includes a valve 310 for selectively admitting a controlled quantity of sample gas, a valve 312 for selectively admitting a controlled quantity of reference gas, and a valve 314 for selectively admitting a controlled quantity of carrier gas. Valves 310, 312, and 314 are individually controllable through a control interface 328 and are selectively enabled and disabled to admit carrier, reference, or sample gases into an injection chamber 320. Note that the valves 310, 312, and 314 may be implemented apart from the micro-miniature gas chromatograph 220 without departing from the intent of the present invention. In the preferred embodiment of the present invention, the valves 310, 312, and 314, and their interconnecting gas-carrying lines are heated by a heating element 330, to minimize the formation of any condensates in the carrier, reference, and sample gases. Other embodiments may omit the heating element 330 without departing from the scope of the present invention.

Micro-miniature fabrication permits the chromatograph 220 to have small interior volumes for its internal gas-carrying pathways, including the injection chamber 320 and a micro-capillary separation column 322. The interior volume of the micro-miniature injection chamber 320 is typically in the micro-liter range. For sample gas BTU content analysis, valve 314 is enabled to begin admitting carrier gas into the injection chamber 320. Subsequently, valve 310 is enabled, admitting sample gas into the injection chamber 320. The carrier gas and sample gas mixture travels through the micro-capillary separation column 322, where the sample gas is separated into its constituents. For system calibration and verification operations, reference gas is used instead of sample gas and the control system (210 in FIG. 2) monitors the output of the micro-miniature gas chromatograph for the expected detection response.

Because gas chromatography separation requires elevated temperatures for both the injection chamber 320 and the micro-capillary separation column 322, heaters 324A and 324B are provided. Heater 324A is in thermal contact with the chamber 320 and heater 324B is in thermal contact with the micro-capillary separation column 322. In the preferred embodiment, the control system (210 in FIG. 2) cooperates with heaters 324A and 324B through the control interface 328 to effect On/Off and set-point temperature control. In the preferred embodiment, the heaters are implemented as thin-film resistive elements disposed on a laminate surface within the micro-miniature gas chromatograph 220 and connected as series elements in current loops monitored by the control system (210 in FIG. 2) through the control interface 328. As the resistance of the heaters is a function of operating temperature, their temperature may be determined by monitoring the voltage drop across heating elements 324A and 324B using a known current, or may be determined by monitoring the current flow resulting from impressing a known voltage across them. Other methods of setting and monitoring the temperature of a resistive temperature element are well known in the art and are considered within the scope of this disclosure. Additionally, the heater elements 324A and 324B may be implemented apart from the integrated micro-miniature gas chromatograph, provided thermal contact is maintained. All such alternate implementations for providing controlled heating of the injection chamber 320 and micro-capillary separation column 322 are considered within the scope of the present invention.

The micro-capillary separation column 322 includes a micro-channel whose interior is coated with an appropriate adsorbent for effecting constituent separation of the sample and reference gases. The separation column 322 includes first and second open ends. The first end of the separation column 322 is in fluid communication with the injection chamber 320 for receiving the gas or mixture of gases flowing from the chamber 320. The second end of the separation column 322 is in fluid communication with a detector 326. The detector detects one or more constituents in the gas mixture exiting from the second end of the separation column 322. The detector 326 provides a detection response signal to the control interface 328, where it is made available to the control system (210 in FIG. 2). Multiple detector types may be used in the present invention, including but not limited to thermal conductivity and optical absorption detectors.

In the preferred embodiment, the chromatograph 220 includes a flow detector depicted as 440 in FIG. 4. In FIG. 4, the flow sensor vents the gas mixture exiting the micro-capillary channel 410 and provides a signal related to sensed flow rate to the control interface 328. The ability to sense flow through the micro-capillary channel 410 allows the chromatograph (220 in FIG. 2) to signal the control system (210 in FIG. 2) when flow rate is reduced, indicating blockage of the channel 410.

Wear Compensation

Figure 4A:
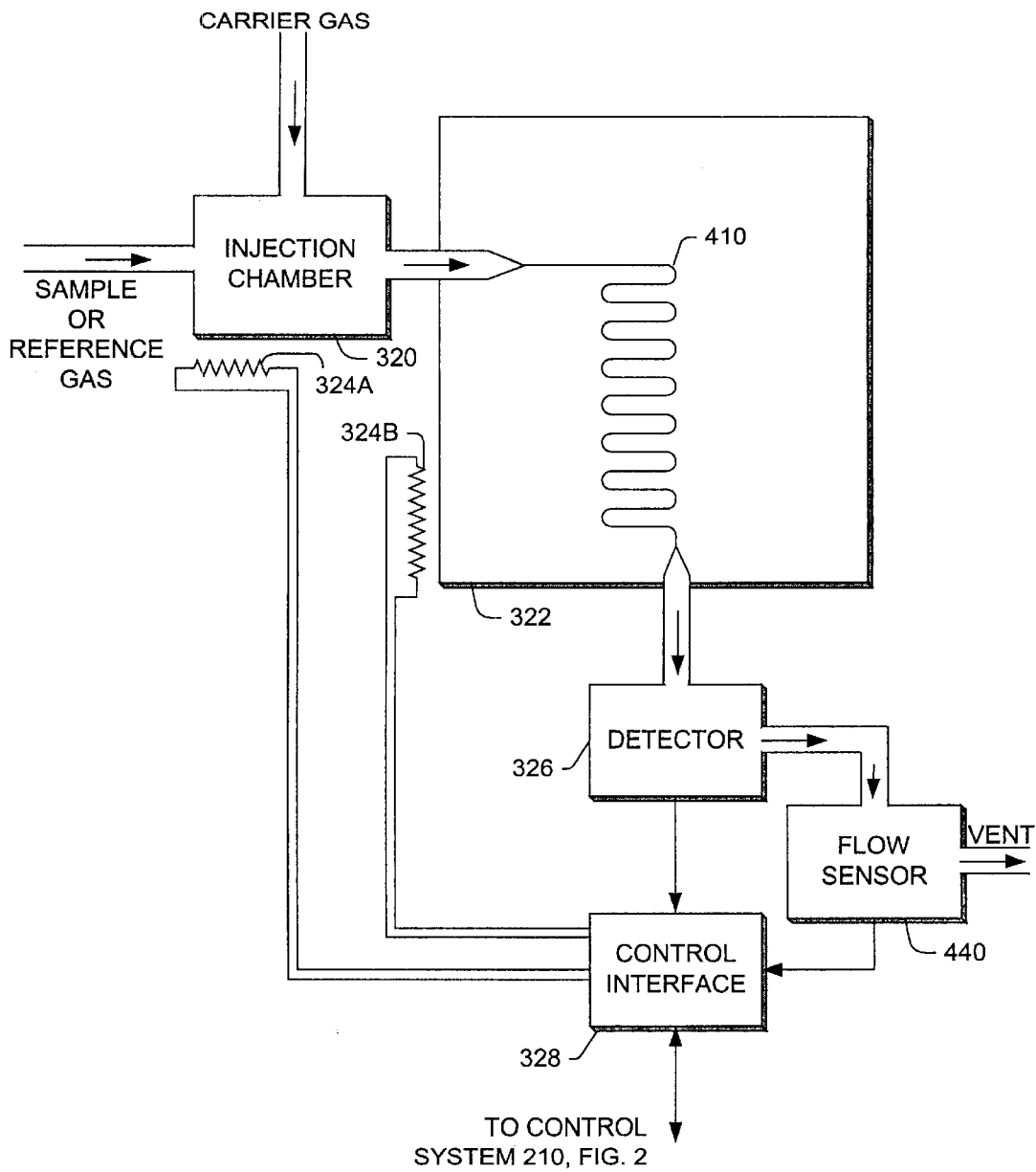
FIG. 4A is a simplified block diagram of the micro-miniature gas chromatograph in the preferred embodiment of the present invention.

Referring to the preferred embodiment shown in FIG. 4A, the adsorbent coating disposed on the interior surface of the micro-capillary channel 410 that forms the basis of the micro-capillary separation column 322 is subject to wear and contamination over time. The energy monitoring system 110 tracks the performance of the micro-miniature gas chromatograph over time using a reference gas analysis and a separation column 322 flow rate determination using a flow rate sensor 440. Because the mole % constituent makeup of the reference gas is known, the control system 210 can correlate observed detection response characteristics or data obtained from the micro-miniature gas chromatograph with known constituent concentrations. This correlation may then be used to compensate the detection response obtained from sample gas having an unknown mole % constituent composition. Further, as contamination accumulates in the micro-capillary separation column 322, the flow rate through the separation column 322 diminishes. Therefore, output from the flow rate sensor 440 may be used to infer the amount of obstruction and, therefore, contamination, in the separation column 322. The flow rate sensor 440 may be designed literally to detect the rate of flow through the separation column 322, or may be designed as a pressure sensor to detect the pressure drop through the separation column 322 as pressure drop through the separation column 322 is directly proportionate to flow restriction.

The energy monitoring system 110 may also be configured to "re-condition" the micro-miniature gas chromatograph 220 at programmable intervals. Re-conditioning entails running a continuous supply of only carrier gas through the micro-capillary separation column 322 for an extended period, while maintaining it at an elevated temperature. Such re-conditioning serves to purge some portion of contaminate accumulation from within the micro-capillary separation column.

Figure 4B:
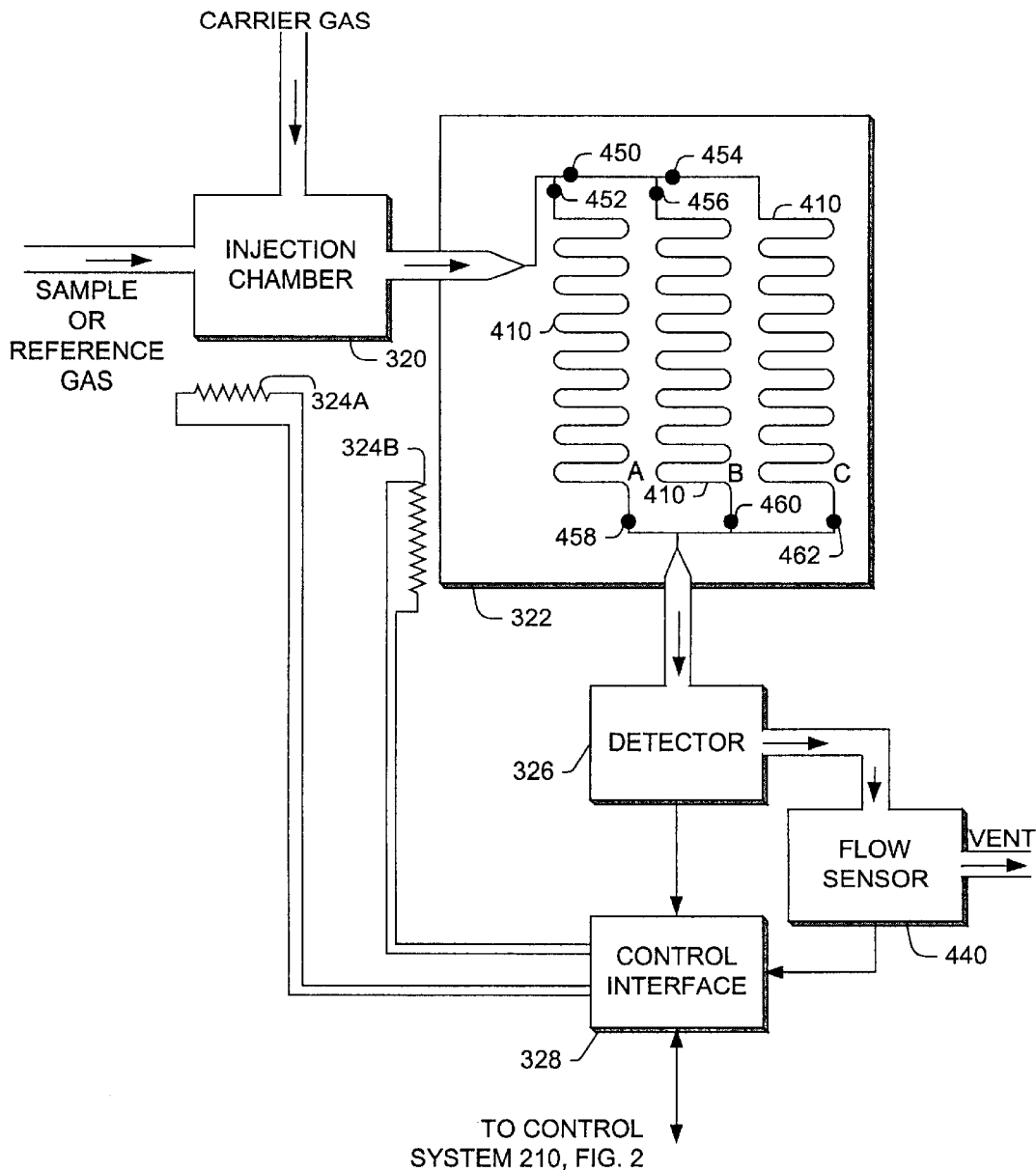
FIG. 4B is a simplified block diagram of the micro-miniature gas chromatograph in a first alternate embodiment of the present invention.

FIG. 4B presents an alternate embodiment of the present invention that provides additional wear compensation measures. In this embodiment, the micro-capillary separation column 322 actually comprises three independent micro-capillary channels 410A, 410B, and 410C. The energy monitoring system 110 initially configures the micro-miniature gas chromatograph 220 to use micro-capillary channel 410A by opening valves 452 and 458, and closing valves 450, 460, and 462. Over time, with repeated analysis cycles, micro-capillary channel 410A becomes contaminated as detected through reference gas analysis and flow-rate sensor 440 indication. At a point where the performance of micro-capillary channel 410A falls below an acceptable level, the energy monitoring system 110 configures the micro-miniature gas chromatograph 220 to operate using micro-capillary channel 410B by opening valves 450,456, and 460, and closing valves 452,454,458 and 462. As with micro-capillary channel 410A, micro-capillary channel 410B becomes contaminated over time and, at a point where the performance of micro-capillary channel 410B falls below an acceptable level, the energy monitoring system 110 configures the gas chromatograph 220 to operate using micro-capillary channel 410C by opening valves 450, 454, and 462, and closing valves 452, 456, 458, and 460. The intent of this alternate embodiment is to provide a plurality of essentially identical micro-capillary channels disposed within the separation column 322, each capable of independently serving as the separation column for gas chromatography operations. Such a plurality of independent separation micro-capillary channels is practical and economical in the micro-miniature gas chromatograph of the present invention. All variations on the number of independent separation columns available are considered within the scope of the present invention. Note that still other embodiments of the present invention may provide multiple micro-capillary separation columns for simultaneous use for enhanced detection capabilities.

Figure 4C:
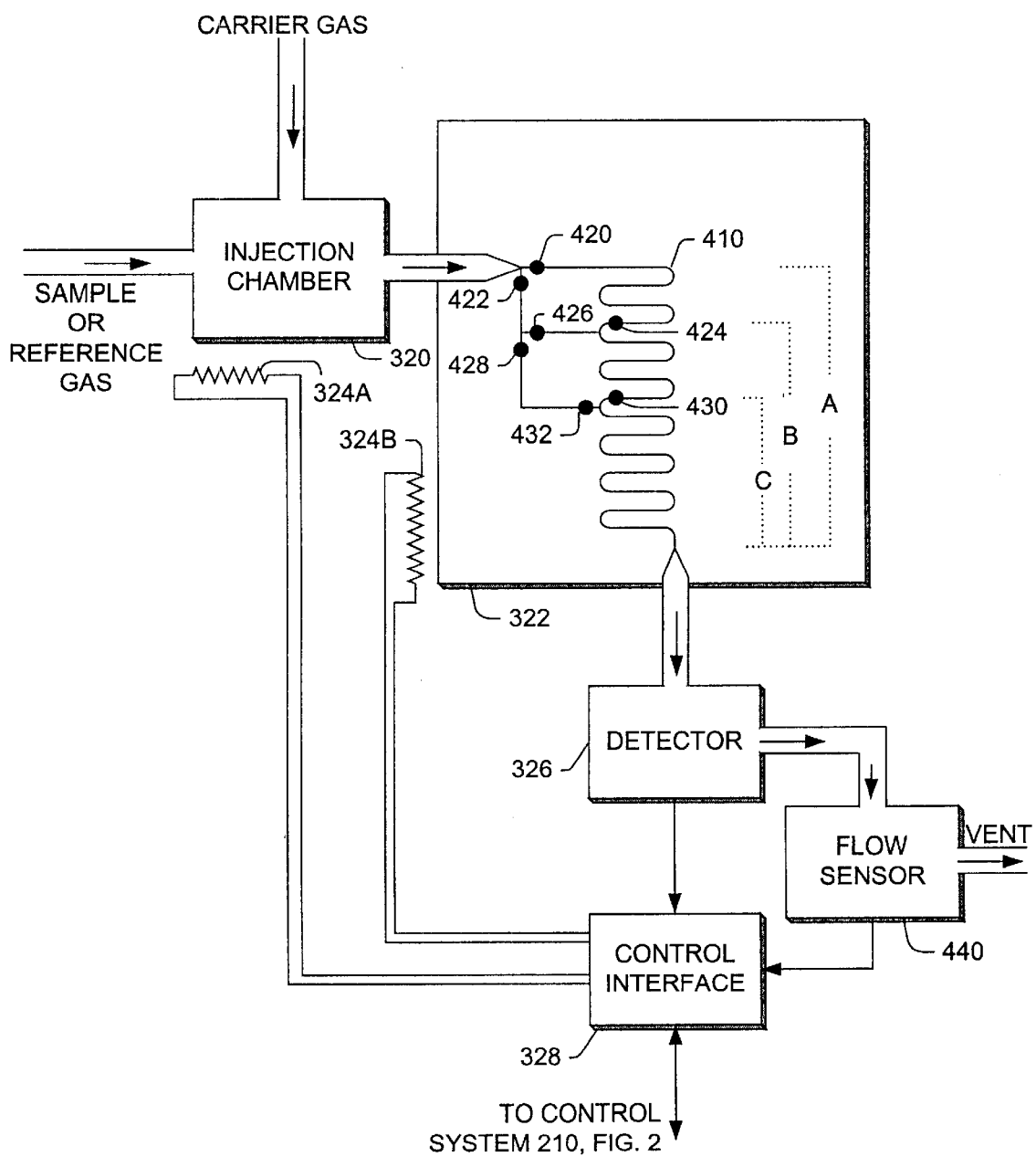
FIG. 4C is a simplified block diagram of the micro-miniature gas chromatograph in a second alternate embodiment of the present invention.

FIG. 4C depicts another embodiment of the present invention with alternate wear compensation measures. In this embodiment of the present invention, the micro-capillary channel 410 is fabricated with added length. A series of micro-miniature valves permit injection of the gas mixture from the injection chamber 320 into different points along the length of channel 410. Initially, valves 420, 424, and 430 are open, and valves 422, 426, 428 and 432 are closed and the entire length "A" of the channel 410 is used. As the initial portion of length "A" becomes contaminated, valve 420 and 424 are closed, valve 422 and valve 426 are opened, valve 430 remains open, and valves 428 and 432 remain closed. This causes the gas mixture from chamber 320 to flow only through length "B" of the channel 410, thereby avoiding flow through the contaminated portion of length A. Similarly, as the initial portion of length B becomes contaminated, valves 426 and 430 are closed and valves 428 and 432 are opened. This causes the gas mixture from chamber 320 to flow only through length "C" of the channel 410, thereby avoiding flow through the contaminated portion of length B. Note that FIGS. 4A–C are not meant to convey the impression that the micro-channel 410 comprising the micro-capillary separation column has significantly smaller dimensions than the other micro-miniature gas conveyance channels disposed throughout the micro-miniature gas chromatograph.

The foregoing details present specific techniques for wear compensation including valve configurations supporting variable length separation columns or independent use of multiple, parallel separation columns, and control system tracking of gas chromatograph separation performance using reference gas. Such specific illustrations are provided for example only and are not meant to limit or exclude various other wear-compensation implementations. All variations of these specific examples are considered within the scope of the present invention.

Programmable Temperature Profiles

Based on supervisory control from the control system, the present invention in one embodiment provides programmable temperature control for the micro-miniature gas chromatograph 220. Sample gas constituent separation speed and detection response is a strong function of the operating temperature of the chromatograph 220, and in particular of operating temperature of the injection chamber 320 and micro-capillary separation column 322.

Sample gas separation may be carried out at a constant temperature, or, based on configuration data modifiable by the energy and flow measurement system end-user, may be carried out using a time varying temperature. The time varying temperature may be a linear ramp that initially begins separation operations at a given temperature and then rises linearly during separation towards a second given temperature. Providing programmable temperature control permits "tuning" the detection response of the chromatograph 220 for specific constituents in the sample gas.

Built-In Self Test

Referring to FIG. 4C, the preferred embodiment of the present invention includes a flow sensor 440. Flow sensor 440 provides an indication of the condition of the micro-capillary channel 410. As noted in the "Wear Compensation" section, analysis of the sample gas can introduce contaminates into the micro-capillary channel 410. Overtime, obstructions can form in the micro-capillary channel 410, or elsewhere in the gas-carrying micro-capillary lines disposed within the micro-miniature gas chromatograph. These obstructions can partially or fully obstruct flow through the micro-capillary separation column 322. Thusly, the flow sensor 440 provides an indication of micro-capillary obstruction and may be implemented as a flow rate sensor for sensing flow through the micro-capillary separation column 322. Additionally, as pressure drop through the micro-capillary separation column 322 is a function of separation column obstruction, a pressure sensor or differential pressure sensor may be used to sense flow through the separation column 322. Reductions in flow rate through separation column 322 below a minimum level result in an error condition for the energy monitoring system 110.

The energy monitoring system of the present invention additionally provides for automatic calibration in the preferred embodiment. Under computer program control, the system 110 may be configured to perform calibration operations at specified time or analysis cycle intervals, or on specified calendar dates. A reference gas having known constituent compositions supports gas chromatograph calibration.

Carrier and Reference Gas Sources

The energy and flow measurement system of the present invention requires carrier gas for conducting gas chromatograph analysis. As previously detailed, consumption of the carrier gas by the present invention's micro-miniature gas chromatograph is minute, typically less than one micro-liter per analysis cycle. As such, the container for holding the pressurized carrier gas can be made quite small in comparison to container sizes required for conventional gas chromatograph system. For example, a conventional gas chromatograph typically consumes 1 ml or more of carrier gas per analysis cycle. To support a significant number of analysis cycles before replenishment of the carrier gas is required, these conventional gas chromatograph systems operate from carrier gas containers having a physical volume of ten or more liters. In contrast, the present invention can operate for extended periods from a carrier gas container having a physical volume of 100 ml or less. In one embodiment of the present invention, the carrier gas container has a length in the range of 6 to 10 cm, and a diameter of 2 to 4 cm. Reference gas, used in system calibration and verification operations, is likewise consumed in minute quantities in the present invention and may be contained in a similarly small container.

Figure 5:
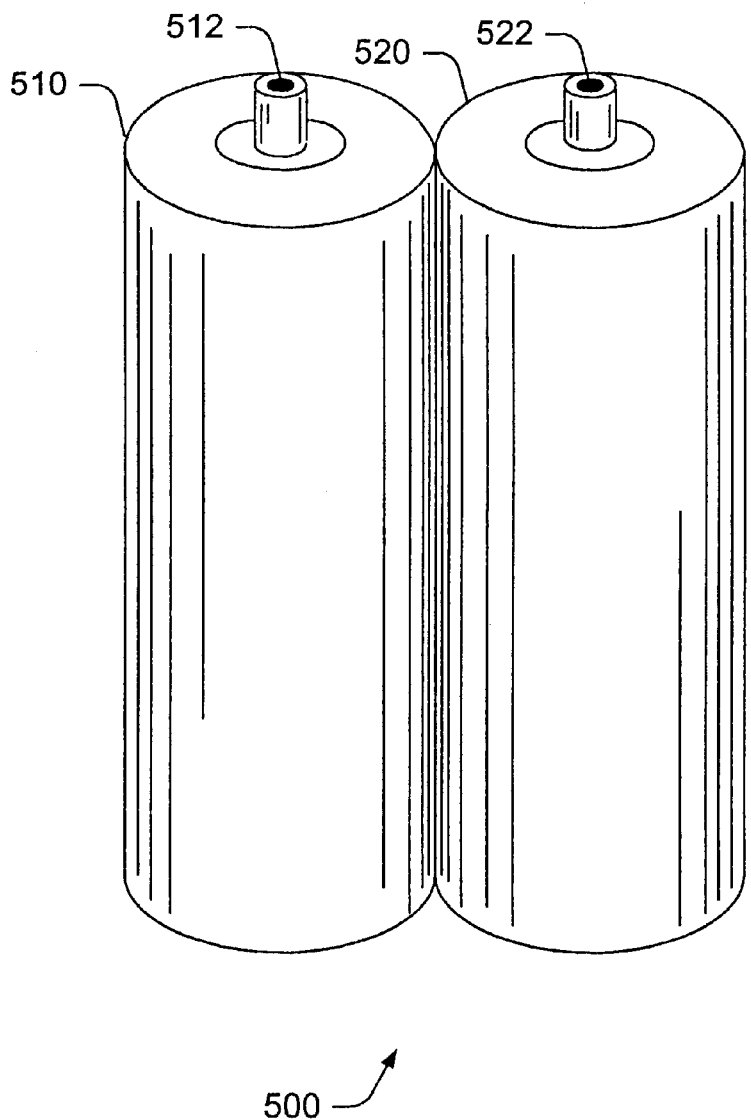
FIG. 5 is a diagram of the carrier and reference gas cartridge in the preferred embodiment of the present invention.

Referring to FIG. 5, one embodiment of the present invention includes a cartridge 500 that provides both a carrier gas pressure vessel 510 and a reference gas pressure vessel 520 joined together. Carrier gas pressure vessel 510 includes a gas outlet 512; likewise reference gas pressure vessel 520 includes a gas outlet 522. Because of its small size, the cartridge assembly 500 may be integrated into the same enclosure housing the electronic and pneumatic subsystems comprising the energy monitoring system 110 without appreciably increasing the volumetric requirements of the enclosure. One embodiment of the system 110 includes a receptacle for automatically receiving and puncturing the cartridge assembly 500. Although depicted as a joined cartridge assembly in FIG. 5, the carrier and reference gas containers may be separate and need not be included in the same enclosure housing the electronic and pneumatic elements of the present invention. Additionally, the cartridge assembly 500 may include other features, such as a built-in pressure indicator useful for determining if a cartridge has adequate gas pressure.

Modularity

Modular design imparts important advantages to the preferred embodiment of the present invention. Referring to FIG. 6, various elements of the energy monitoring system 110 that are subject to wear or consumption are designed to allow modular replacement. The primary modular items include an analysis module 610 comprising the gas cartridge assembly 500, the conditioner 230, and the micro-miniature gas chromatograph 220. The gas sampler 250 is also designed as a replaceable module.

In the preferred embodiment, the energy monitoring system 110 and its analysis module 610 are designed such that the analysis module 610 plugs into the energy monitoring system 10 in convenient fashion, allowing easy removal and replacement of the entire analysis module. Further modularity is imparted to the energy monitoring system 110 in its preferred embodiment through modular design of the analysis module. The analysis module 610 provides a receptacle that is designed to allow the gas cartridge assembly 500 to be inserted and removed in a manner that provides automatic mating of the gas-tight connections required between the gas cartridge 500 and the conditioner 230. The analysis module 610 also provides a receptacle designed to allow easy insertion and removal of the conditioner 230, again with features providing automatic mating of the gas tight connections between the conditioner 230, the gas cartridge 500, the gas sampler 250, and the micro-miniature gas chromatograph 220. Finally, the analysis module 610 provides an additional receptacle designed to allow convenient insertion and removal of the micro-miniature gas chromatograph with support for automatically mating with the gas tight interconnects between the micro-miniature gas chromatograph 220 and the conditioner 230. Although the preferred embodiment supports plug-in insertion and removal of various sub-systems within the analysis module, the invention may be practiced with greater or lesser modularity. For example, the analysis module may not be replaceable as a group and the gas-carrying interconnections between the gas cartridge assembly 500, the conditioner 230, and the micro-miniature gas chromatograph 220 may require manual connection. All such variations on modularity are considered within the scope of the present invention.

Because of the unique characteristics of the micro-miniature gas chromatograph 220, including its high level of functional integration, its cost is greatly reduced from a conventional packed-column gas chromatograph assembled from various mechanical and electromechanical parts. Because of this cost reduction, it is economically viable to treat the micro-miniature gas chromatograph 220 as a disposable element. This disposability, combined with the modularity of design, reduces field service and inventory costs.

Monitors

The energy monitoring system 110 uses a plurality of monitors to measure key parameters of the flowing natural gas necessary for volume and energy measurement. In the preferred embodiment, monitored parameters include the pressure, temperature, and flow rate of the flowing natural gas. In FIG. 2, a temperature monitor 240B is in thermal communication with the flowing natural gas and provides an analog signal proportionate to the flowing gas temperature. Other devices or methods may be used to obtain the temperature of the natural gas flowing within the pipeline, and are all within the spirit of the present invention.

For monitor flowing gas pressure, the preferred embodiment of the present invention uses a general-purpose pressure transducer such as the PDCR 800 manufactured by Druck Inc., having a business address at 4 Dunham Drive New Fairfield, Conn. 06812, and a web site at www.druck.com. Various other methods are suitable for measuring the pressure of the natural gas flowing within the pipeline, including electro-mechanical, optical, and acoustical apparatus. All such devices are within the scope of the present invention.

For flow rate, the preferred embodiment of the present invention is adapted to interface with a positive displacement gas meter, having an output drive or signal proportionate to the amount of gas passing through it. As noted earlier, many other mechanisms are available that provide an output signal proportionate to the flow rate of a gas. Such mechanisms include electromechanical displacement sensors, acoustic sensors, vibratory sensors, and opto-electronic sensors. Any such device providing an output signal proportionate to flow rate is considered within the spirit of the present invention.

What is claimed is:

1. An apparatus for monitoring an energy value for a flowing gas comprising:
   a flow monitor for measuring a flow rate of the flowing gas;
   a micro-miniature gas chromatograph for detecting an amount of a constituent bearing on energy content of the flowing gas comprising:
   i. a micro-capillary injection chamber in selective fluid communication with an inert carrier gas and a sample of the flowing gas for mixing the carrier gas and the sample into a gas mixture,
   ii. a micro-capillary separation column for separating the constituent from the gas mixture having a first opening in fluid communication with said injection chamber for receiving the gas mixture and a second opening for exhausting the constituent separated from the gas mixture,
   iii. a detector in fluid communication with said second opening of said separation column for detecting an amount of the constituent, and
   iv. a heater in thermal communication with said injection chamber and said separation column for heating said injection chamber and said separation column;
   a control system operatively associated with said flow monitor and said detector for calculating the energy value of the flowing gas based on the flow rate of the flowing gas and the detected amount of the constituent;
   an inlet tube in fluid communication with the flowing gas for obtaining the sample; a pressure regulator operatively associated with the sample tube for regulating the pressure of the sample;
   a filter operatively associated with the pressure regulator for filtering the sample;
   an outlet tube in fluid communication with said micro-miniature gas chromatograph for conveying the regulated and filtered sample gas to said micro-miniature gas chromatograph; and
   a heater in thermal communication with at least one of said inlet tube, said filter, said pressure regulator, and said outlet tube for preventing condensates from forming in the sample gas.

2. The apparatus of claim 1 wherein said micro-miniature gas chromatograph is detachably connected as a replaceable module.

3. The apparatus of claim 1 wherein said micro-miniature gas chromatograph further comprises:
   a plurality of micro-capillary separation columns disposed in parallel connection between said injection chamber and said detector; and
   a plurality of micro-miniature valves disposed within the said plurality of separation columns and operatively associated with said control system for allowing the control system to selectively isolate one of the said plurality of separation columns for separating the constituent in the gas mixture.

4. The apparatus of claim 1 wherein said micro-miniature gas chromatograph further comprises:
  a plurality of gas-conveying interconnections between said injection chamber and said micro-capillary separation column for injecting the gas mixture into one of a plurality of points disposed along the length of said separation column; and
  a plurality of micro-miniature valves disposed within said gas-conveying interconnections operatively associated with said control system for allowing said control system to select one of the plurality of injection points for injecting the gas mixture into the separation column.

5. The apparatus of claim 1 further comprising a gas cartridge separately containing the carrier gas and a reference gas for use by said gas chromatograph.

6. The apparatus of claim 5 wherein said gas cartridge is detachably connected as a replaceable module.

7. The apparatus of claim 5 wherein said control system, said micro-miniature gas chromatograph, said flow monitor, and said gas cartridge are commonly housed within an environmental enclosure.

8. The apparatus of claim 1 further comprising a conditioner disposed in advance of said micro-miniature gas chromatograph having separate filtering and pressure regulation for the carrier gas, the sample gas, and a reference gas for providing conditioned carrier, reference, and sample gases to said micro-miniature gas chromatograph.

9. The apparatus of claim 8 wherein said conditioner is detachably connected as a replaceable module.

10. The apparatus of claim 1 further comprising a gas sampler which is detachably connected for modular replacement.

11. The apparatus of claim 1 wherein operating power for said apparatus is supplied by an external solar panel.

12. The apparatus of claim 1 wherein said detector detects a plurality of constituent gases, including nitrogen, oxygen, methane, ethane, propane, butane, pentane, and selected hexanes.

13. The apparatus of claim 12 wherein the BTU value is determined by said control system based on a mole % concentration of detected constituent gases separated from the sample using the micro-miniature gas chromatograph.

14. The apparatus of claim 12 wherein a supercompressibility value is determined by said control system based on a mole % concentration of detected constituent gases.

15. The apparatus of claim 1 further comprising a gas cartridge for supplying the carrier gas and a sealed enclosure housing said gas chromatograph, said injection chamber, and said gas cartridge.

16. The apparatus of claim 1 wherein at least a portion of said gas chromatograph is a replaceable module detachably connected to adjacent sections of said gas chromatograph.

17. The apparatus of claim 16 wherein said separation column is within said replaceable module.

18. The apparatus of claim 16 wherein said injection chamber is within said replaceable module.

19. The apparatus of claim 1 wherein said control system is configured to periodically operate in a wake state to calculate the energy value of the flowing gas and an ultra-low power sleep state in between wake states.

20. The apparatus of claim 19 including a battery for supplying power for operation.

21. The apparatus of claim 20 further including a solar panel for supplying power for operation and to charge said battery.

22. The apparatus of claim 1 wherein a conditioner is placed prior to said chromatograph within said energy monitoring apparatus for filtering the sample gas prior to said injection chamber.

23. The apparatus of claim 1 wherein said carrier gas line of a conditioner prior to said chromatograph further includes a pressure regulator for reducing the pressure associated with the carrier gas prior to said injection chamber.

24. The apparatus of claim 1 wherein said carrier gas line of a conditioner prior to said chromatograph further includes a second pressure regulator for reducing the pressure associated with the carrier gas prior to said injection chamber.

25. The apparatus of claim 1 further comprising a supply of reference gas wherein said injection chamber is in selective fluid communication with said supply of reference gas and said control system is configured to inject the carrier gas and the sample gas during a first operation and inject the reference gas during a second operation.

26. The apparatus of claim 1 further comprising a second heater adjacent said injection chamber for heating said gas mixture.

27. The apparatus of claim 1 further comprising a second heater adjacent micro-capillary channels other than said separation column for heating gases flowing through portions of said gas chromatograph.

28. The apparatus of claim 1 wherein said gas chromatograph further comprises a second detector associated with said second opening of said separation column for detecting an amount of a second constituent separated from said flowing gas in said separation column.

29. The apparatus of claim 1 wherein said gas chromatograph further comprises a plurality of detectors associated with said second opening of said separation column for detecting an amount of a plurality of constituents separated from said flowing gas in said separation column.

30. The apparatus of claim 29 wherein individual ones of said detectors are configured to detect a constituent of the group consisting of: nitrogen, oxygen, methane, ethane, propane, butane, pentane, and hexane.

31. The apparatus of claim 1 wherein said control system is configured to determine supercompressibility of the constituent based on the amount of the constituent detected by said detector.

32. An apparatus for measuring an energy value for a flowing gas comprising:
  a flow monitor for monitoring a flow rate of the flowing gas;
  a pressure monitor for monitoring a pressure of the flowing gas;
  a temperature monitor for monitoring a temperature of the flowing gas;
  a gas sampler for obtaining a sample from the flowing gas;
  a gas cartridge separately containing a carrier gas and a reference gas;
  a gas conditioner for conditioning the carrier gas, the reference gas, and the sample;
  a micro-miniature gas chromatograph for detecting an amount of a constituent of the sample bearing on energy content of the flowing gas comprising:
    i. a micro-capillary injection chamber in selective fluid communication with an inert carrier gas and the sample for mixing the carrier gas and sample into a gas mixture,
    ii. a micro-capillary separation column having a first opening in fluid communication with said chamber for receiving the gas mixture and a second opening for exhausting the constituent separated from the gas mixture, iii. a detector in fluid communication with said second opening of said separation column for detecting an amount of the constituent, and iv. a heater in thermal communication with said injection chamber and said separation column for heating said injection chamber and said separation column;

a control system operatively associated with said flow, temperature, and pressure monitors, said gas sampler, said gas conditioner, and said micro-miniature gas chromatograph for determining the energy value for the flowing gas based on the flow rate of the flowing gas, the temperature of the flowing gas, the pressure of the flowing gas, and the detected amount of the constituent; and wherein the combination of said control system, said micro-miniature gas chromatograph, and said flow meter require less than 2W of power in operation.

33. The apparatus of claim 32 wherein said gas cartridge, said gas conditioner, and said micro-miniature gas chromatograph are combined in a separately replaceable analysis module.

34. The apparatus of claim 32 wherein said gas cartridge, said gas conditioner, and said micro-miniature gas chromatograph comprising a replaceable analysis module are independently replaceable modular assemblies.

35. The apparatus of claim 32 wherein a common environmental enclosure houses said pressure monitor, said temperature monitor, said gas sampler, said gas cartridge, said gas conditioner, said micro-miniature gas chromatograph, and said control system.

36. The apparatus of claim 32 wherein an external solar power panel provides operating power for said apparatus.

37. An apparatus for monitoring an energy value for a flowing gas comprising:

a flow monitor for measuring a flow rate of the flowing gas;

a replaceable, micro-miniature gas chromatograph module for detecting amounts of constituents bearing on energy content of the flowing gas comprising:

i. a micro-capillary injection chamber in selective fluid communication with an inert carrier gas and a sample of the flowing gas for mixing the carrier gas and the sample into a gas mixture, ii. a micro-capillary separation column for separating the constituent from the gas mixture having a first opening in fluid communication with said injection chamber for receiving the gas mixture and a second opening for exhausting the constituent separated from the gas mixture, iii. a plurality of detectors associated with said second opening of said separation column for detecting an amount of a plurality of constituents separated from said flowing gas in said separation column, and iv. a heater in thermal communication with said injection chamber and said separation column for heating said injection chamber and said separation column;

a control system operatively associated with said flow monitor and said detectors for calculating the supercompressibility of the flowing gas based on the flow rate of the flowing gas and the detected amount of the constituents to determine an energy value for the flowing gas; and wherein said control system is configured to determine the mole percent of the constituent based on the amount of the constituent detected by said detector.

* * * * *